US008668722B2

(12) United States Patent  (10) Patent No.: US 8,668,722 B2
Pavlov et al.  (45) Date of Patent: Mar. 11, 2014

(54) METHOD FOR LOCKING AN ARTIFICIAL FACET BETWEEN TWO VERTEBRAL BODIES

(71) Applicants: Paul Pavlov, Nijmegen (NL); Robert Frigg, Oberdorf (CH); Beat Lechmann, Oberdorf (CH)

(72) Inventors: Paul Pavlov, Nijmegen (NL); Robert Frigg, Oberdorf (CH); Beat Lechmann, Oberdorf (CH)

(73) Assignee: DePuy Synthes Products, LLC, Raynham, MA (US)

( * ) Notice: Subject to any disclaimer, the term of this patent is extended or adjusted under 35 U.S.C. 154(b) by 0 days.

(21) Appl. No.: 13/675,511

(22) Filed: Nov. 13, 2012

(65) Prior Publication Data

US 2013/0116732 A1 May 9, 2013

Related U.S. Application Data (63) Continuation of application No. 12/716,631, filed on Mar. 3, 2010, now Pat. No. 8,317,839, which is a continuation of application No. 11/126,976, filed on May 10, 2005, now Pat. No. 7,699,878, which is a continuation of application No. PCT/CH02/00608, filed on Nov. 13, 2002.

(51) Int. Cl.
  *A61B 17/88* (2006.01)
  *A61B 17/70* (2006.01)
(52) U.S. Cl.
  USPC .................... 606/279; 606/247; 623/17.11
(58) Field of Classification Search
  USPC ........ 411/411, 315–323; 606/86 R, 104, 232, 606/246–248, 279, 300–321, 323, 325–328, 606/331, 907, 105, 916; 623/17.11–17.16
  See application file for complete search history.

(56) References Cited

U.S. PATENT DOCUMENTS

| | | | |
|---|---|---|---|
| 4,754,749 A | 7/1988 | Tsou | |
| 6,077,267 A | 6/2000 | Huene | |
| 6,123,711 A | 9/2000 | Winters | |
| 6,358,254 B1 | 3/2002 | Anderson | |
| 6,485,518 B1 | 11/2002 | Cornwall et al. | |
| 6,524,316 B1 | 2/2003 | Nicholson et al. | |
| 6,540,747 B1 | 4/2003 | Marino | |
| 6,547,795 B2 | 4/2003 | Schneiderman | |
| 6,974,478 B2 * | 12/2005 | Reiley et al. | 623/17.11 |
| 7,699,878 B2 | 4/2010 | Pavlov et al. | |
| 8,317,839 B2 | 11/2012 | Pavlov et al. | |
| 2001/0007074 A1 | 7/2001 | Strobel et al. | |
| 2002/0151895 A1 * | 10/2002 | Soboleski et al. | 606/61 |
| 2003/0212400 A1 | 11/2003 | Bloemer et al. | |
| 2005/0240188 A1 | 10/2005 | Chow et al. | |

FOREIGN PATENT DOCUMENTS

EP  0857465  8/1998
WO  WO 2004/043278  5/2004

* cited by examiner

*Primary Examiner* — Nicholas Woodall
*Assistant Examiner* — Larry E Waggle, Jr.
(74) *Attorney, Agent, or Firm* — Baker & Hostetler LLP (57) ABSTRACT

A bone screw (1) is used for locking an articular facet between the superior and inferior articular processes of two vertebral bodies and is provided with a threaded shaft (2), a screw head (3) and a central axis (4). The screw head (3) is further provided with a number of grooves (5) on the periphery of the screw head (3) which run essentially parallel to said central axis (4).

17 Claims, 7 Drawing Sheets

METHOD FOR LOCKING AN ARTIFICIAL FACET BETWEEN TWO VERTEBRAL BODIES

CROSS REFERENCE TO RELATED APPLICATIONS

This application is a continuation of U.S. patent application Ser. No. 12/716,631, filed Mar. 3, 2010, which is a continuation of U.S. patent application Ser. No. 11/126,976, filed May 10, 2005, which is a continuation of International Patent Application No. PCT/CH2002/000608, filed Nov. 13, 2002, the entire contents of which are incorporated herein by reference thereto.

TECHNICAL FIELD

This invention concerns a bone screw, in particular for locking an articular facet between the superior and inferior articular processes of two vertebral bodies.

BACKGROUND

To achieve a circumferential arthrodesis (fusion) the anterior and the posterior columns must be treated. The goal of the treatment is the restoration of the lordotic curve and the anatomically correct disc space. Anteriorly, i.e. in the intervertebral space, implants like cages are inserted after disc removal. The posterior vertebral column, where the articular facet is located, should be locked as well. State-of-the-art techniques consider translaminar screws or transpedical instrumentation which, however, are not satisfactory.

Translaminar screws have certain disadvantages, like a) the screw insertion point is difficult to localize; the localization is done under full view, i.e. a separate posterior incision is performed medially whereas muscles must be separated from spinal and laminar processes. Most morbidity results from medial incision; b) the surgeon's view is two-dimensional due to the small incision which may result in interference of the second screw with the first one; and c) aiming devices or navigation tools did not improve insertion technique or precision of screw placement.

From U.S. Pat. No. 2001/007074 A1 STROBEL a bone screw is known.

From U.S. Pat. No. 4,754,749 TSOU another bone screw is known which has two closed canals in the screw head at an angle with the screw axis. A guide pin is insertable in one of these closed canals, so that upon insertion of the guide pin it projects radially over the shaft and axially over the head of the screw which renders it complicated and rather unstable.

The invention as claimed aims at solving the above described problems.

SUMMARY

The present invention provides a bone screw and a method for locking an articular facet of a vertebral body.

The advantages of said method and the use of said bone screw are the following: percutaneous approach which results in reduced morbidity; low implant cost due to simple design, in particular in comparison to transpedicular fixation; lower risk with regard to screw positioning compared to translaminar screws; and easy removal of the screws.

The interference screw according to the invention allows a new surgical technique to lock the articular facets of vertebral bodies.

The natural functional spine unit (FSU) contains two articular facets. The function of the screw according to the invention is the interference in the sense of obstruction or fixation of said articular facets. Since the core diameter of the screw is significantly larger than the gap in the articular facet, the device is hindering the natural articulation. The function of the screw thread is the insertion by rotation. After insertion the screw thread protects the screw from axial migration and the anti-rotation device protects the screw from migration by rotation.

According to the new surgical method the locking screws are inserted through two percutaneous approaches in the trajectories parallel to the articular surface of the articular facet. Aiming wires guarantee the correct positioning. An anti-rotation element keeps the bone screw in position and hinders the screws from turning out if micro-motion is applied to the screws. This technique is applicable if the anterior vertebral column (i.e. the intervertebral space of the related segment) is stabilized with a spacer such as an intervertebral cage.

According to a special embodiment the grooves on the periphery of the screw head are running essentially parallel to the central axis. This shall be interpreted in such a way that minor angulation with regard to the central axis either towards radially the latter or tangentially to it would still be functional. Such an angulation in a radial plane and measured relative to the central axis might be in the order of up to 60°, but preferably lees than 20°. The possible angulation in a tangential plane and measured relative to the central axis might be in the order of maximum 20°, preferably less than 10°.

In a particular embodiment the bone screw is provided with at least one pair of diametrically opposed grooves on the periphery of said screw head which enhances stability of the implant.

The screw head may be provided with a central cavity coaxially arranged with respect to said central axis, e.g. with a polygonal profile, preferably a hexagonal profile for receiving a screw-driver having a corresponding profile.

The grooves on the periphery of the screw head may be juxtaposed to the polygonal planes of said central cavity. By this measure a higher mechanical strength can be achieved.

In a further embodiment an anti-rotation element is insertable in said groove or said pair of grooves on the periphery of said screw head, whereby said anti-rotation element in its inserted position projects radially out of the periphery of said screw head. The anti-rotation element is preferably a U-shaped staple with two legs and a central portion bridging said two legs and designed for insertion into said groove or said pair of grooves of said screw head. The anti-rotation element has preferably a diameter which is larger than said screw head. The anti-rotation element in form of a U-shaped staple may be provided with a guiding element attached to said central portion and running essentially parallel to said legs. The guiding element may be in the form of a plate, a circular cylinder or a prism designed for insertion into said central cavity of said screw head. The cylindrical shape of the guiding element has the advantage of a more accurate gliding.

The central portion of the anti-rotation element may be provided with at least one perforation for removal of the screw.

The threaded shaft of the bone screw has preferably a thread with a high angle of pressure, e.g. in the range of 4° to 70°. The flank of said thread can be symmetrically or asymmetrically oriented. The asymmetrically oriented thread is compressing particularly cancellous bone. This increases initial fixation stability.

The bone screw may be self-tapping, preferably by means of a cutting edge.

The core of the screw shaft may be either cylindrical or tapering away from the screw head.

In the case of cylindrical core of the screw shaft various advantages can be achieved, namely: a continuous bending strength along the screw shaft; the application of a constant insertion torque while turning the screw in the articular facet; and due to the constant shaft diameter the screw does not become loose if the device is turned back slightly after insertion.

This could appear if the surgeon brings the grooves for the anti-rotation element in congruent direction like the articular facet gap.

In the case of a conical shape of the core the shaft is compressing the surrounding bone. This increases the initial stability of the implant.

The envelope of the threaded shaft may be cylindrical allowing also a constant insertion torque. However, the envelope of the threaded shaft preferably tapers away from the screw head so that the purchase of the thread in the bone is increasing by turning the screw in.

The bone screw may be self-drilling, preferably by means of a chucking groove.

The new method for locking an articular facet between the superior and inferior articular processes of two vertebral bodies consists in the insertion of the threaded shaft of a bone screw in the gap of said articular facet. To that purpose the bone screw is preferably cannulated and insertion is performed by means of an aiming wire. The bone screw has preferably a screw head with a larger diameter than said threaded shaft and said threaded shaft is inserted in said gap of said articular facet until said screw head touches the bone. Upon insertion of said bone screw an anti-rotation element may be applied to said screw head such that rotation of said bone screw is prevented.

The various features of novelty which characterize the invention are pointed out with particularity in the claims annexed to and forming part of this disclosure. For the better understanding of the invention, its operating advantages and specific objects attained by its use, reference should be had to the accompanying drawings, examples and descriptive matter in which are illustrated and described preferred embodiments of the invention.

DETAILED DESCRIPTION OF ILLUSTRATIVE EMBODIMENTS

Figure 1:
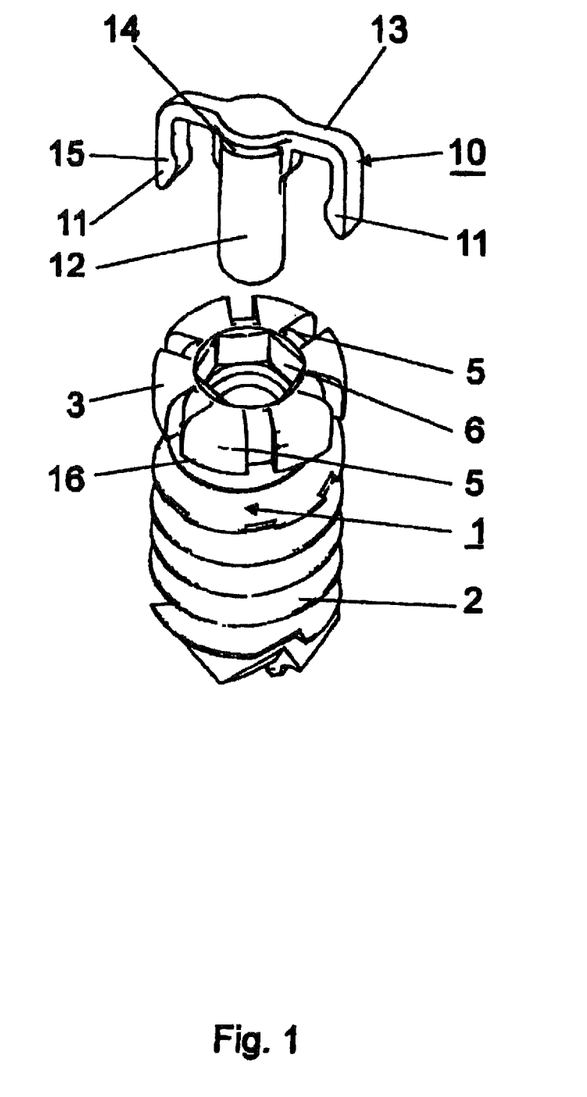
FIG. 1 is a perspective view of the bone screw according to the invention together with an anti-rotation element to be used with the screw.
Figure 2A:
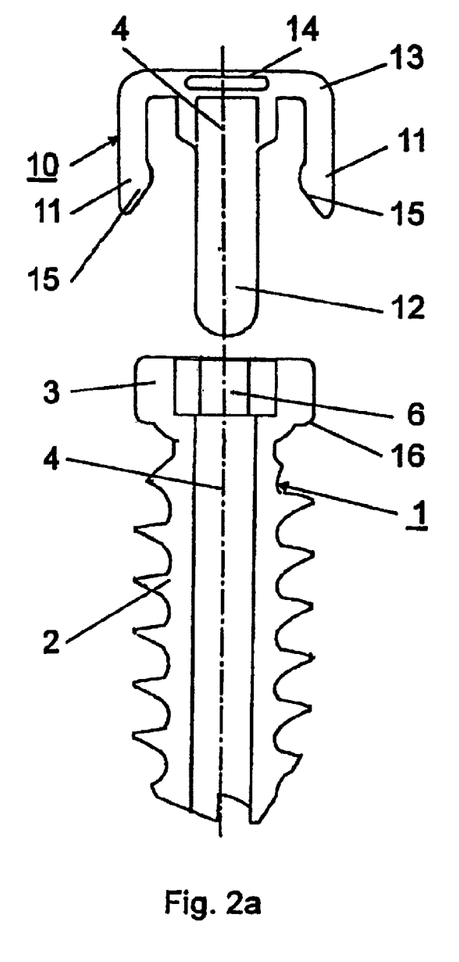
FIG. 2a is a longitudinal section through the central axis of the screw and the anti-rotation element according to FIG. 1.
Figure 2B:
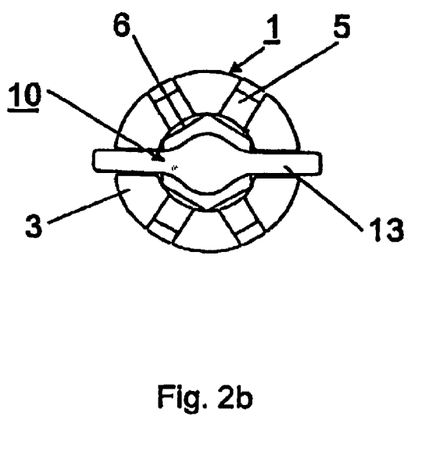
FIG. 2b is a top view of the bone screw according to FIG. 1 with the anti-rotation element inserted into the screw head.

The bone screw 1 as represented in FIGS. 1, 2a and 2b is used in particular for locking an articular facet between the superior and inferior articular processes of two vertebral bodies. It has a threaded shaft 2, a screw head 3 and a central axis 4. The screw head 3 is provided with six grooves 5 regularly disposed on the periphery of the screw head 3 running essentially parallel to the central axis 4. The screw head 3 is further provided with a central cavity 6 coaxially arranged with respect to the central axis 4 and having a hexagonal shape.

The anti-rotation element 10 is provided with a U-shaped staple having two legs 11 and a central portion 13 bridging said two legs 11. The U-shaped staple is provided with a guiding element 12—having the shape of a circular cylinder—attached to the central portion 13 and running essentially parallel to the legs 11. As can be seen in FIGS. 1 and 2a the anti-rotation element 10 may be connected to the bone screw 1 by moving it along the central axis 4 whereby its central portion 13 enters the central cavity 6 of the screw head 3 and the two legs 11 are inserted into one of the three pairs of grooves 5 of the screw head 3 as shown in FIG. 2b.

The free ends of the two legs 11 are provided with an protrusion 15 oriented radially inwards to the central axis 4 so that when the legs 11 are gliding along the grooves 5 the protrusions 15 will click under the lower edge 16 of the screw head 3 thereby securing the anti-rotation element 10 against withdrawal in the opposite axial direction.

The central portion 13 of the U-shaped staple is further provided with at a perforation 14 facilitating removal of the bone screw 1.

Useful materials for the bone screw 1 as well as for the anti-rotation element 10 are titanium, titanium alloys or fiber-reinforced plastic materials. They may be coated with ceramic.

A detailed method of operation follows for the better understanding of the invention:

1. Both positions in extension of the articulating planes of the articular facet concerned are identified and marked accordingly on the skin. To this purpose an image intensifier is used to control position and direction.

2. Bilateral skin incisions are performed in the direction of the articular facets.

Figure 3:
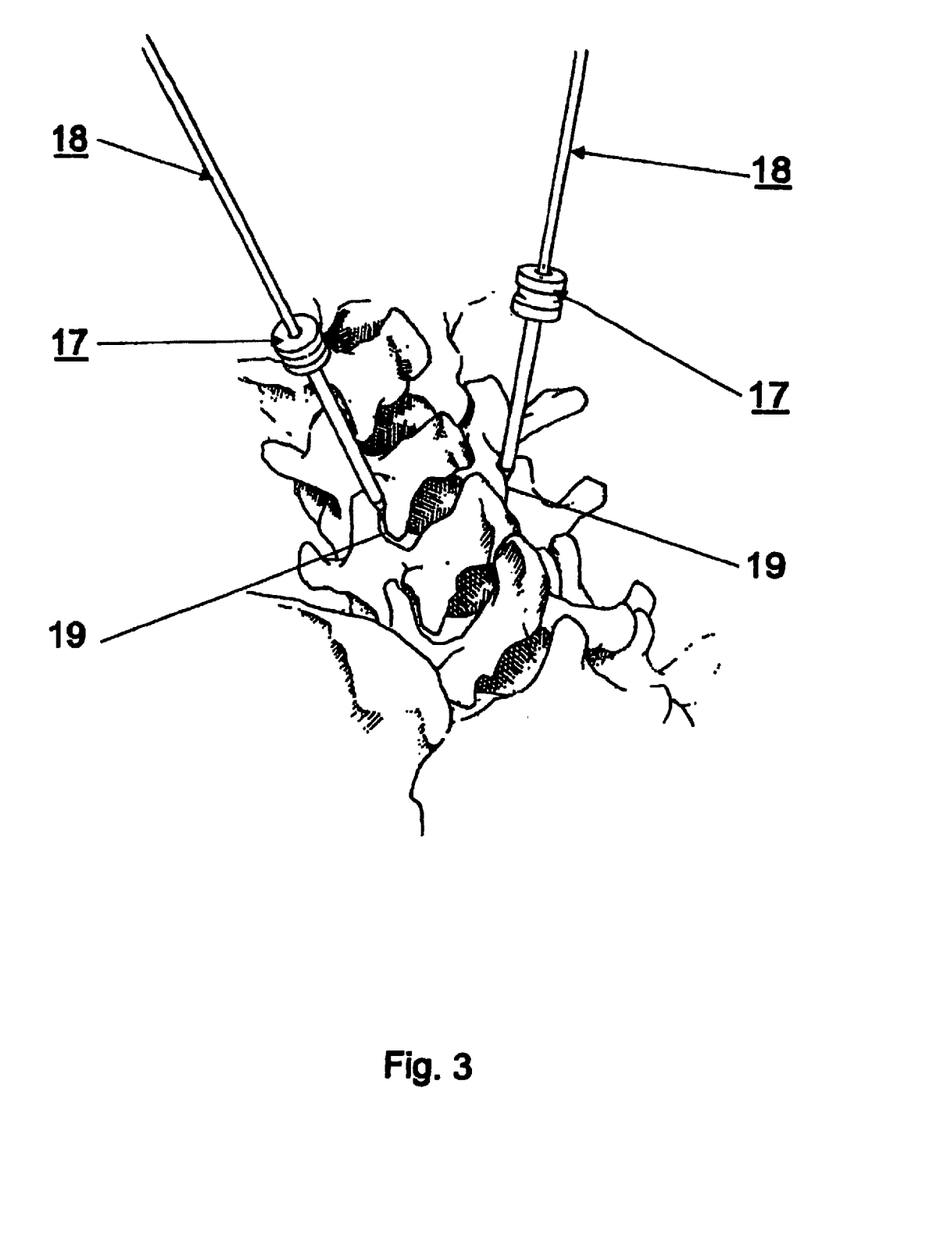
FIG. 3 is a perspective view of a trocar for bringing an aiming wire into the gap between the articular facet.

3. Depending on the surgeon's preference, a trocar 17 or similar instrument is used to bring an aiming wire 18 into the gap 19 between the articular facets (FIG. 3). Positional control is indicated using an image intensifier.

Figure 4:
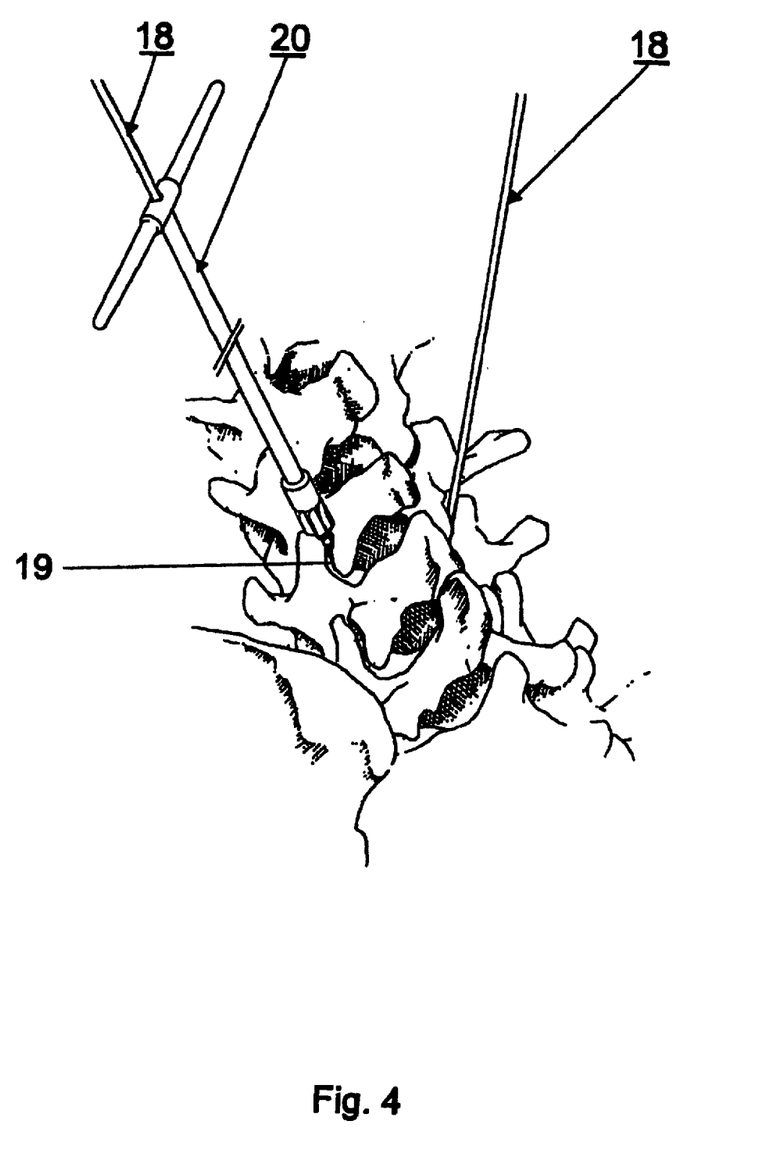
FIG. 4 is a perspective view of a drill bit, the aiming wires being temporarily fixed in the gaps of the articular facets.

4. As shown in FIG. 4 the aiming wires 18 are temporarily fixed in the gaps 19 of the articular facets by means of the drill bit 20 ("screw head reamer" or "counter sink").

Figure 5:
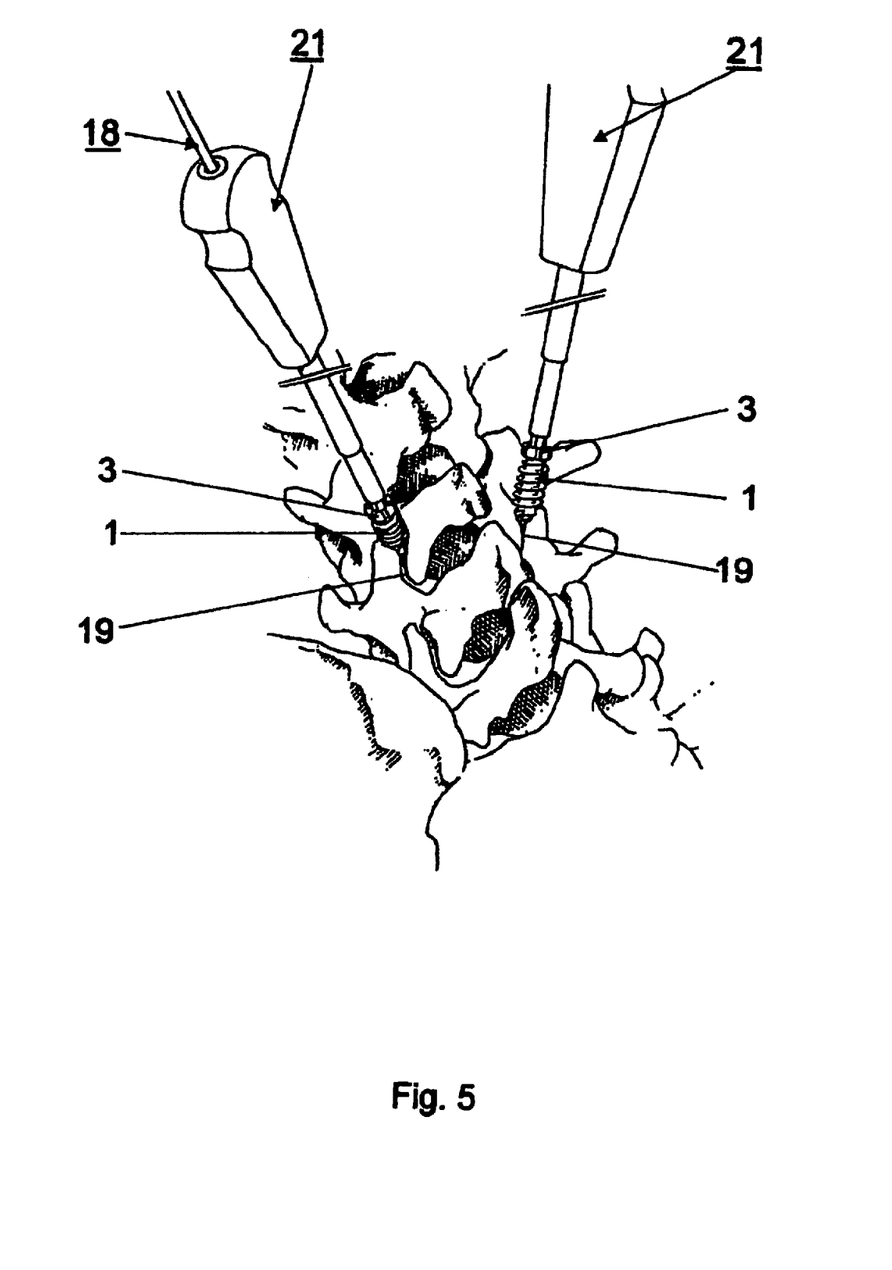
FIG. 5 is a perspective view of the bone screw being inserted by means of a screw-driver into the gap of the articular facet by using the temporarily fixed guiding wire.

5. As shown in FIG. 5 a cannulated and self-tapping bone screw 1 is inserted by means of a screwdriver 21 into the gap 19 by using the temporarily fixed guiding wires 18 until the screw heads 3 of the bone screws 1 are touching the bone.

Figure 6:
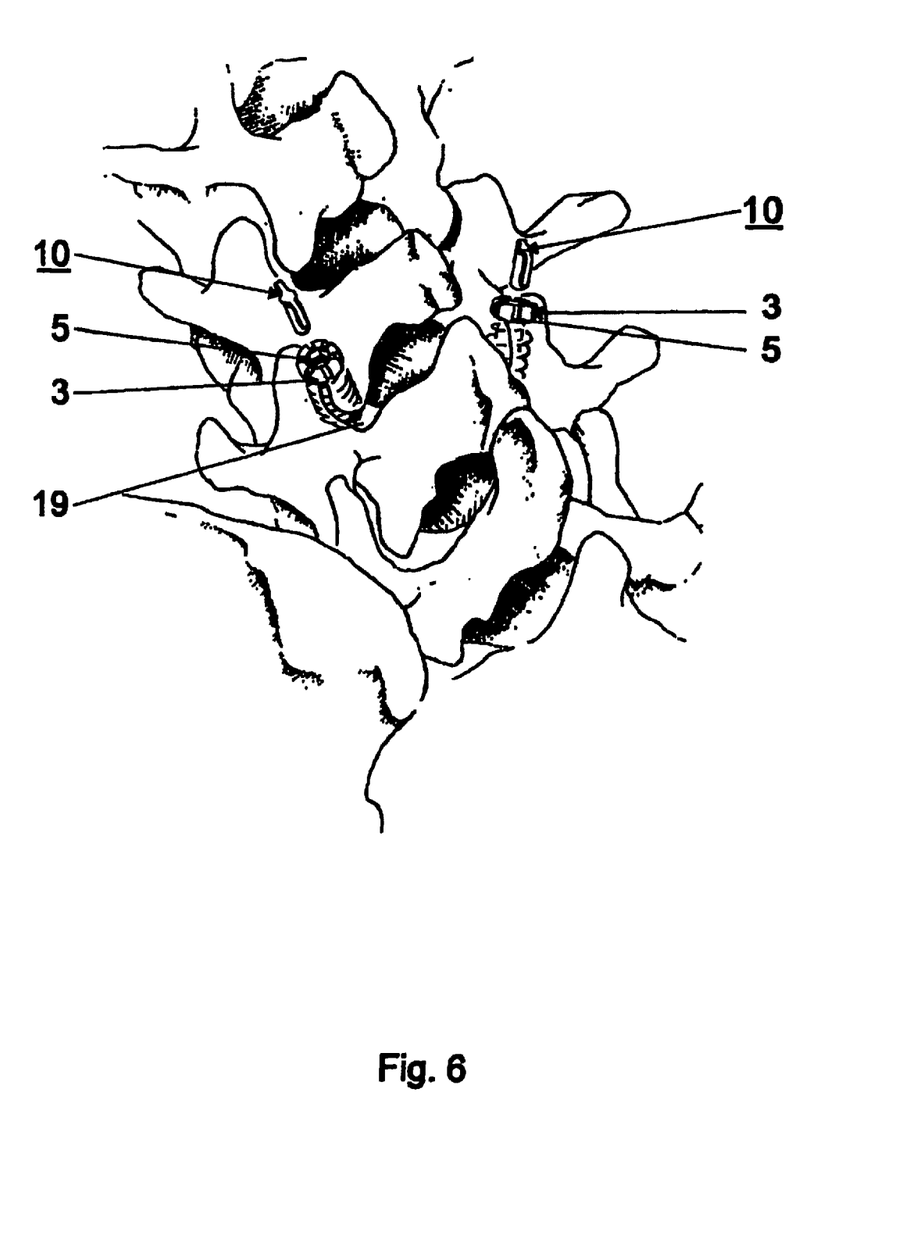
FIG. 6 is a perspective view of the anti-rotation element being put over the screw head into its grooves closest to the joint gap.
Figure 7:
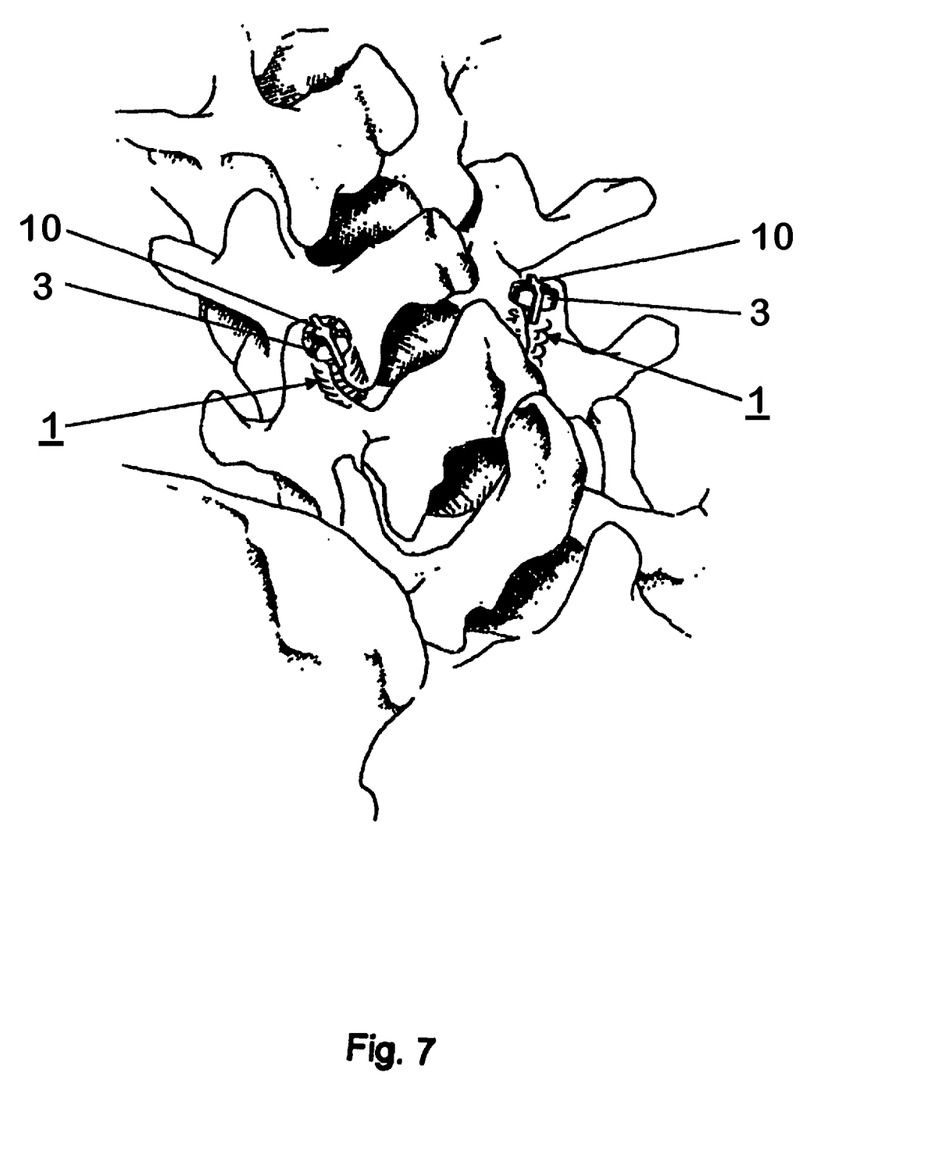
FIG. 7 is a perspective view of the inserted bone screw to which the anti-rotation element has been attached.

6. As shown in FIG. 6 an anti-rotations element 10 is put over the screw head 3 in the grooves 5 (notches) closest to the joint gap 19. Eventually the bone screw 1 must be turned back by some degrees in order to match the grooves 5 (notches) in the screw head 3 with the joint gap 19 (FIG. 7).

7. All instruments are removed.

8. The placement of the bone screws 1 is verified by using an image identifier and the wound is closed.

The method of operation as described can be performed on one side of the vertebral column only but is preferably performed simultaneously on the right and left side, as shown in FIGS. 3 to 7, which has biomechanical advantages.

What is claimed:

1. A method of inserting an implant into a facet joint defined between an inferior articular surface of a superior vertebra and superior articular surface of an inferior vertebra, the method comprising:
   inserting a surgical instrument into the facet joint;
   after the inserting step, guiding a reamer along the surgical instrument and into the facet joint, and reaming the inferior and superior articulating surfaces with the reamer; and
   after the reaming step, inserting an implant at least partially into the facet joint defined by an inferior articular surface of the superior vertebra and a superior articular surface of the inferior vertebra, the implant having a body that is elongate along a central axis, wherein the inserting step includes the steps of (1) at least partially engaging the implant with both the inferior and superior articular surfaces, and (2) locating the central axis between the inferior and superior articular surfaces.

2. The method of claim 1, further comprising, wherein the first inserting step comprises separating the inferior articular surface from the superior articular surface.

3. The method of claim 1, wherein the reamer comprises a drill bit, and the reaming step further comprises guiding the drill bit along the surgical instrument and into the facet joint.

4. The method of claim 3, wherein the surgical instrument comprises a wire, and the step of inserting a surgical instrument into the facet joint comprises inserting the wire into the facet joint.

5. The method of claim 1, further comprising, after the reaming step, the step of removing the surgical instrument from the facet joint.

6. The method of claim 1, further comprising the step of guiding the implant into the facet joint along the surgical instrument.

7. The method of claim 1, further comprising the step of securing the implant to an insertion tool before the step of inserting the implant.

8. The method of claim 7, further comprising, after the step of reaming, the step of causing the insertion tool to drive the implant into the facet joint.

9. The method of claim 8, further comprising the step of releasing the implant from the insertion tool after the implant has been inserted into the facet joint.

10. The method of claim 1, wherein the inserting step comprises screwing the implant into the facet joint.

11. The method of claim 1, wherein the inserting step comprises substantially aligning the central axis with both the inferior articular surface and the superior articular surface.

12. The method of claim 1, wherein the surgical instrument comprises a wire, and the step of inserting a surgical instrument into the facet joint comprises inserting the wire into the facet joint.

13. A method of inserting an implant into a facet joint between an inferior articular surface of a superior vertebra and a superior articular surface of an inferior vertebra, the method comprising:
   separating the inferior articular surface from the superior articular surface by inserting a surgical instrument into the facet joint;
   reaming the inferior and superior articular surfaces by guiding a drill bit along the surgical instrument and into the facet joint;
   inserting an implant at least partially into the facet joint such that the implant engages both the inferior articular surface and the superior articular surface, wherein the inserting step includes the step of guiding the implant along the surgical instrument and into the facet joint.

14. The method of claim 13, wherein the implant has a body that is elongate along a central axis, and wherein the inserting step includes the step of substantially aligning the central axis with both the inferior articular surface and the superior articular surface.

15. A method of inserting a first implant into a first facet joint between a superior vertebra and an inferior vertebra, and a second implant into a second facet joint between the superior vertebra and the inferior vertebra, the method comprising:
   inserting the first implant at least partially into the first facet joint defined by a first inferior articular surface of the superior vertebra and a first superior articular surface of the inferior vertebra, the first implant having a first body that is elongate along a first central axis, wherein the inserting step includes the steps of (1) at least partially engaging the first implant with both the inferior and superior articular surfaces, and (2) locating the first central axis between the inferior and superior articular surfaces; and
   inserting the second implant at least partially into the second facet joint of the superior and inferior vertebrae, the second facet joint defined by a second inferior articular surface of the superior vertebra and a second superior articular surface of the inferior vertebra, the second implant having a second body that is elongate along a second central axis, wherein the step of inserting the second implant includes the steps of (1) at least partially engaging the second implant with both the second inferior articular surface and the second superior articular surface, and (2) locating the second central axis between the second inferior articular surface and the second superior articular surface.

16. The method of claim 15, further comprising the steps of:
   reaming the second inferior articular surface and the second superior articular surface by guiding a drill bit along a surgical instrument and into the second facet joint;
   securing the second implant to an insertion tool before the step of inserting the second implant; and
   causing the insertion tool to drive the implant into the facet joint.

17. The method of claim 16, further comprising, prior to the reaming step, the step of separating the second inferior articular surface from the second superior articular surface by inserting the surgical instrument into the second facet joint.

* * * * *